United States Patent [19]
Gold et al.

[11] Patent Number: 4,808,573
[45] Date of Patent: Feb. 28, 1989

[54] CARBOXYALKYL DIPEPTIDES AND ANTI-HYPERTENSIVE USE THEREOF

[75] Inventors: Elijah H. Gold; Bernard R. Neustadt, both of West Orange; Elizabeth M. Smith, Verona, all of N.J.

[73] Assignee: Schering Corporation, Kenilworth, N.J.

[21] Appl. No.: 29,293

[22] Filed: Mar. 23, 1987

Related U.S. Application Data

[63] Continuation-in-part of Ser. No. 258,484, Apr. 28, 1981, abandoned, which is a continuation-in-part of Ser. No. 201,649, Oct. 28, 1980, abandoned, which is a continuation-in-part of Ser. No. 199,886, Oct. 23, 1980, abandoned.

[30] Foreign Application Priority Data

Oct. 15, 1981 [EP] European Pat. Off. ........ 81108348.4

[51] Int. Cl.$^4$ .................. A61K 31/40; C07D 207/16
[52] U.S. Cl. .................................. 514/19; 514/423; 548/553; 548/492
[58] Field of Search ............... 548/533, 492; 514/412, 514/423, 19

[56] References Cited

U.S. PATENT DOCUMENTS

| | | | |
|---|---|---|---|
| 4,350,704 | 9/1982 | Hoefle et al. | 546/147 X |
| 4,374,829 | 2/1983 | Harris et al. | 514/21 |
| 4,508,729 | 4/1985 | Vincent et al. | 514/419 |

FOREIGN PATENT DOCUMENTS 0049658 4/1982 European Pat. Off. ............ 548/492

*Primary Examiner*—David B. Springer
*Attorney, Agent, or Firm*—Anita W. Magatti; James R. Nelson; Stephen I. Miller

[57] ABSTRACT

The present invention relates to carboxyalkyl dipeptides which are inhibitors of angiotensin-converting enzyme and are useful as antihypertensive agents and in the treatment of congestive heart failure.

The compounds of the present invention are compounds of the formulae

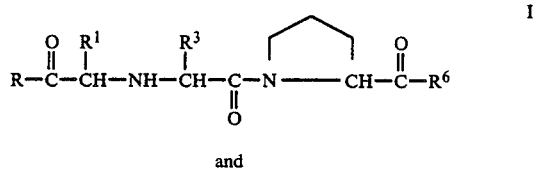

I and

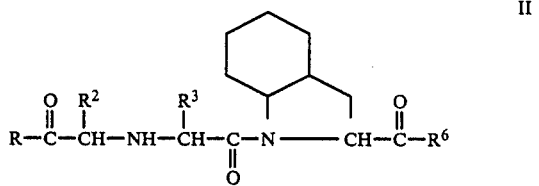

II and the pharmaceutically acceptable salts thereof, wherein
R and $R^6$ are the same or different and are hydroxy or lower alkoxy;
$R^1$ is benzyloxylower alkyl or benzylthiolower alkyl;
$R^2$ is benzylthiomethyl, 2-phenylethylthiomethyl, naphthylmethylthiomethyl, methylbenzylthiomethyl; 2-(carboxyphenyl)ethyl or 2-(alkoxycarbonylphenyl)ethyl; and
$R^3$ is hydrogen, lower alkyl or aminolower alkyl.

14 Claims, No Drawings

CARBOXYALKYL DIPEPTIDES AND ANTI-HYPERTENSIVE USE THEREOF

This application is a continuation-in-part of Ser. No. 258,484, filed Apr. 28, 1981, now abandoned, which is a continuation-in-part of Ser. No. 201,649, filed Oct. 28, 1980, now abandoned, which is a continuation-in-part of Ser. No. 199,886, filed Oct. 23, 1980, now abandoned.

The present invention relates to carboxyalkyl dipeptides which are useful as inhibitors of angiotensin-converting enzyme and as antihypertensive agents.

The compounds of the present invention are compounds of the formulae

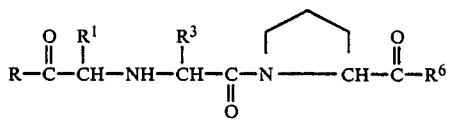

and

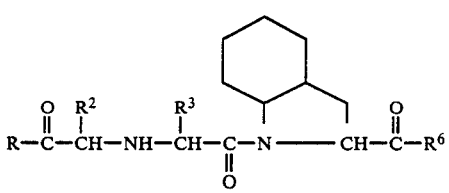

and the pharmaceutically acceptable salts thereof, wherein

R and $R^6$ are the same or different and are hydroxy or lower alkoxy;

$R^1$ is benzyloxylower alkyl or benzylthiolower alkyl;

$R^2$ is methylbenzylthiomethyl, carboxyphenylethyl or alkoxycarbonylphenylethyl; and $R^3$ is hydrogen, lower alkyl or aminolower alkyl.

The aforementioned compounds of formulae I and II, as defined above, include all possible stereoisomers. The term "lower alkyl" refers to straight and branched hydrocarbon chains of from one to six carbon atoms, for example, methyl, ethyl, propyl, isopropyl, butyl, isobutyl, t-butyl, pentyl or hexyl. "Alkoxy" similarly refers to alkoxy groups of 1 to 6 carbon atoms.

Preferred compounds of formula I and II are those wherein $R^3$ is lower alkyl, with methyl being more preferred. Also preferred are compounds of formulae I and II wherein $R^6$ is hydroxy. Another group of preferred compounds of formulae I and II are those wherein R is lower alkoxy with ethoxy being more preferred.

Preferred compounds of formula I are those wherein the lower alkyl portion of $R^1$ is methyl.

Preferred compounds of formula II are those wherein the alkoxy portion of the alkoxycarbonylphenylethyl group is ethoxy. Also preferred are compounds of formula II wherein the substituent on the phenyl ring is in the para position, i.e., wherein $R^2$ is p-methylbenzylthiomethyl, p-carboxyphenylethyl or p-(ethoxycarbonyl)phenylethyl.

Preferred compounds of the present invention are:

N-(1(R)-ethoxycarbonyl-2-benzylthioethyl)-(R,S)-alanyl-(S)-proline,

N-(1(S)-ethoxycarbonyl-2-benzyloxyethyl)-(R,S)-alanyl-(S)-proline,

1-[N-(1(R)-ethoxycarbonyl-2-(4-methylbenzylthio)ethyl]-(R,S)-alanyl]-cis,syn-perhydroindole-2(S)-carboxylic acid, 1-[N-[1(S)-ethoxycarbonyl-3-(4-ethoxycarbonylphenyl)propyl]-(S)-alanyl]-cis,syn-perhydroindole-2(S)-carboxylic acid, 1-[N-[1(S)-carboxy-3-(4-carboxyphenyl)propyl]-(S)-alanyl]-cis,syn-perhydroindole-2(S)-carboxylic acid, and the hydrochloride salts thereof.

The compounds of the present invention can be produced by several methods, two of which are depicted in the following equations. Reactive groups not involved in the condensations described below such as amino, carboxy, mercapto, etc., may be protected by methods standard in peptide chemistry prior to the coupling reactions and subsequently deprotected to obtain the desired products. Such reactions are demonstrated in the Examples.

Method 1, Route 1

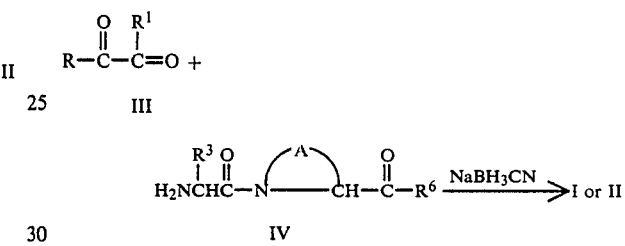

wherein R, $R^1$, $R^3$ and $R^6$ are as defined above completes a proline or perhydroindole ring.

Keto acid (or ester) III is condensed with dipeptide IV in aqueous solution, optimally near neutrality, or in a suitable organic solvent (for example, CH$_3$OH) in the presence of sodium cyanoborohydride to give I or II. Alternatively, the intermediate Schiff base, enamine, or aminol may be catalytically reduced to yield product I or II, for example, by hydrogen in the presence of 10% palladium on carbon or of Raney nickel. The ratio of diasteriomeric products formed may be altered by choice of catalyst.

Alternatively III can be condensed with an mino acid V.

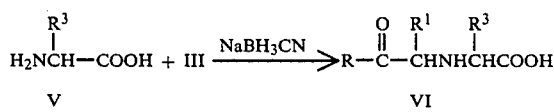

under the same conditions to yield amino acid VI. Subsequent coupling by known methods with amino acid derivative VII gives I or II.

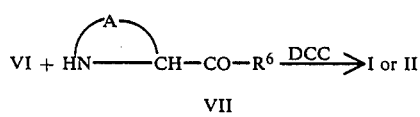

The known methods encompass reactive group protection during the coupling reaction, for example, by N-formyl N-t-butoxycarbonyl and N-carbobenzyloxy groups followed by their removal to yield I or II. Furthermore, the R function may include removable ester groups such as benzyl, ethyl or t-butyl. Condensing agents in this synthetic route are typically those useful in peptide chemistry such as dicyclohexylcarbodiimide (DCC) or diphenylphosphoryl azide (DPPA) or VI may be activated via the intermediacy of active esters such as that derived from 1-hydroxybenzotriazole (HOBT).

Route 2

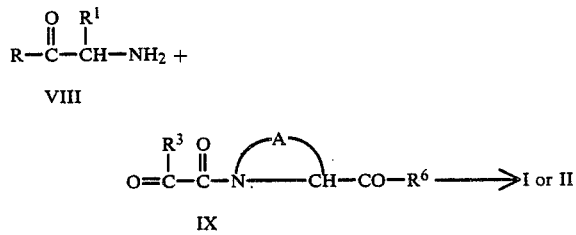

Amino acid (or ester) VIII is condensed with ketone IX under conditions described for Route 1 to give I or II Method II, Route 1

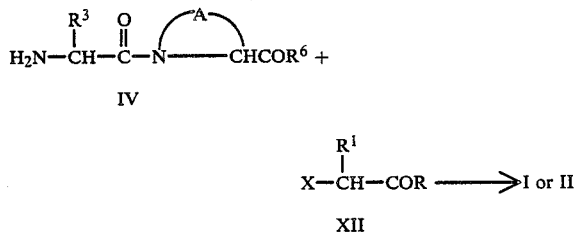

The dipeptide IV is alkylated with the appropriate alpha-haloacid (or ester) or alpha-sulfonyloxy acid (or ester) XIII, wherein X is chlorine, bromine, iodine, alkanesulfonyloxy or arenesulfonyloxy, under basic conditions in water or in an organic solvent.

Alternatively, the synthesis can be performed in a step-wise fashion.

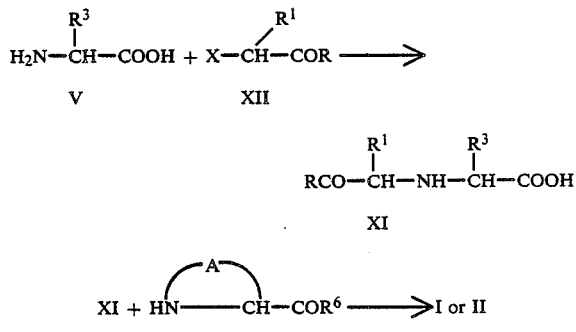

In this stepwise synthesis, X in the compound of formula XII is chlorine, bromine, iodine, alkanesulfonyloxy or arenesulfonyloxy.

The aminoacid V (or a protected ester form thereof, such as t-butyl or benzyl ester) is alkylated by the alpha-haloacid (or ester) or alpha-sulfonyloxy acid (or ester) XII under basic conditions to yield (following ester deprotection, if necessary) compounds XI. This is condensed by standard methods as indicated under Route 1 with the aminoacid (ester or amide) VII to afford I or II.

The starting materials which are required for the above processes herein described are known in the literature or can be made by known methods from known starting materials.

In the compounds of formulae I and II, the carbon atoms to which $R^1$ and $COR^6$ are attached may be asymmetric. The compounds accordingly exist in diastereoisomeric forms or in mixtures thereof. The above described syntheses can utilize racemates, enantiomers or diastereomers as starting materials. Enantiomeric intermediates may be obtained by resolution methods known in the art. When diastereomeric products result from the synthetic procedures, the diastereomeric products can be separated by conventional chromatographic or fractional crystallization methods.

In general, the aminoacid part-structures, i.e.,

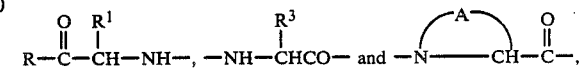

wherein R, $R^1$, $R^3$ and are as defined above, are preferred in the configuration most similar to that of natural L-amino acids. Usually, natural L-amino acids are assigned to the S-configuration. A notable exception is the natural amino acid L-cysteine which is assigned to the R-configuration.

The compounds of this invention form salts with various inorganic and organic acids and bases which are also within the scope of the invention. Such salts include ammonium salts, alkali metal salts like sodium and potassium salts (which are preferred), alkaline earth metal salts like the calcium and magnesium salts, salts with organic bases e.g., dicyclohexylamine salts, N-methyl-D-glucamine, salts with amino acids like arginine, lysine and the like. Also, salts with organic and inorganic acids may be prepared, e.g., HCl, HBr, $H_2SO_4$, $H_3PO_4$, methanesulfonic acid, toluenesulfonic acid, maleic acid, fumaric acid and camphorsulfonic acid. The nontoxic physiologically acceptable salts are preferred, although other salts are also useful, e.g., in isolating or purifying the product.

The salts may be formed by conventional means, as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

The following examples illustrate the preparation of the compounds of the present invention. The diastereomers prepared as set forth below may be isolated by column chromatography or by fractional crystallization.

EXAMPLE 1

N-(1(R)-Ethoxycarbonyl-2-benzylthioethyl)-(R,S)-alanyl-(S)-proline hydrochloride Mix S-benzyl-L-cysteine ethyl ester hydrochloride (8.28 g) with $NaHCO_3$ solution until basic. Extract with dichloromethane, dry with $MgSO_4$, and concentrate to dryness at room temperature. Dissolve the residue in tetrahydrofuran (80 ml) containing pyruvoyl-L-proline (2.1 g) and 5 Angstrom molecular sieves (4 g). Stir for 2 days and then add, dropwise over 4 hours, a solution of sodium cyanoborohydride in ethanol (20 ml). Stir for 18 hours, filter, and concentrate the filtrate to dryness. Partition the residue between water and dichloromethane. Absorb the aqueous phase on a sulfonic acid ion exchange resin and elute with 4% pyridine in water. Concentrate to dryness. Dissolve the residue in a mixture of methanol (5 ml) and ether (1500 ml). Acidify this solution with 3.5M HCl in ether and filter the resulting precipitate to obtain the title compound (2.5 g), m.p. 90°–100° C. and $[\theta]_D^{26} = -73.4°$ (1%, H$_2$O).

EXAMPLE 2

N-(1(S)-Ethoxycarbonyl-2-benzyloxyethyl)-(R,S)-alanyl-(S)-proline hdyrochloride

Following the procedure of Example 1, react O-benzyl-L-serine ethyl ester hydrochloride (5 g) with pyruvoyl-L-proline (1.26 g) to yield the title compound (1.6 g), m.p. 90°–100° and $[\theta]_D^{26} = -71.3°$ (1%, H$_2$O).

EXAMPLE 3

1-[N-[1(R)-Ethoxycarbonyl-2-methylbenzylthioethyl]-(R,S)-alanyl]-cis,syn-perhydroindole-2(S)-carboxylic acid Following the procedure of Example 1, substitute S-4-methylbenzyl-L-cysteine ethyl ester for S-benzyl-L-cysteine ethyl ester and substitute N-pyruvoyl-(S)-perhydroindole for N-pyruvoyl-L-proline to obtain the title compound, m.p. 55°–60° C.

EXAMPLE 4

1-[N-[1(S)-Ethoxycarbonyl-3-(4-ethoxycarbonylphenyl)propyl]-(S)-alanyl]-cis,syn-perhydroindole-2(S)-carboxylic acid Step 1. 2-Bromo-4-(4-carboxyphenyl)butyric acid: Heat ethyl 2-bromo-4-(4-cyanophenyl)butyrate (16.5 g) in 47–49% hydrobromic acid (160 ml) under reflux for 16 hr. Cool the reaction mixture and dilute with ice to give the title compound, a light tan solid (15.07 g), m.p. 172°–176°.

Step 2. Ethyl 2-bromo-4-(4-ethoxycarbonylphenyl)butyrate: Combine the product of Step 1 (15.07 g), 1,3-dicyclohexylcarbodiimide (22.0 g) and 4-dimethylaminopyridine (1.28 g) in dichloromethane (CH$_2$Cl$_2$) (150 ml) and treat with absolute ethanol (20 ml) at 0°–5° C. and stir for 18 hr. Filter the reaction mixture and concentrate the filtrate in vacuo. Place the residue on a column of silica gel (3 L) and elute with hexane:EtOAc 9:1 to give the title compound, a yellow oil (16.90 g).

Step 3. N-[1(R)- and 1(S)-Ethoxycarbonyl-3-(4-ethoxycarbonylphenyl)propyl]-(S)-alanine t-butyl esters: Heat the product of Step 2 (16.90 g) and (S)-alanine t-butyl ester hydrochloride (8.05 g) in dimethylformamide (DMF) (80 ml) and triethylamine (40 ml) at 70° for 20 hr. Concentrate the reaction mixture in vacuo and partition the residue between ethyl acetate (EtOAc) and H$_2$O. Dry (MgSO$_4$) the EtOAc and concentrate in vacuo to give an amber oil (15.86 g). Chromatograph the mixture (8.0 g) on Waters Prep 500 (2 cartridges) using hexane:ethyl acetate 19:1 and 9:1 to give N-[1(R)-ethoxycarbonyl-3-(4-ethoxycarbonylphenyl)propyl]-(S)-alanine t-butyl ester, a pale yellow oil (1.08 g), $[\alpha]_D^{26} = -21.6°$ (MeOH) and N-[1(S)-ethoxycarbonyl-3-(4-ethoxycarbonylphenyl)propyl]-(S)-alanine t-butyl ester, a pale yellow oil (1.42 g), $[\alpha]_D^{26} = -4.6°$ (MeOH) and overlaps (0.1 g).

Step 4. N-[1(S)-Ethoxycarbonyl-3-(4-ethoxycarbonylphenyl)propyl]-(S)alanine: Treat N-[1(S)-ethoxycarbonyl-3-(4-ethoxycarbonylphenyl)propyl]-(S)-alanine t-butyl ester (2.81 g) in CH$_2$Cl$_2$ (40 ml) at 0°–5° with trifluoroacetic acid (TFA) (30 ml). Stir the resulting mixture at 0°–5° for 0.5 hr., warm to room temperature and stir for 6 hr. Concentrate the reaction mixture in vacuo and chromatograph the residue on a column of silica gel (2 L), eluting with CHCl$_3$:i-PrOH:7% NH$_4$OH (1:1:1, organic phase) to give the title compound, a white solid (2.06 g), m.p. 145°–147°, $[\alpha]_D^{26} = -33.7°$ (MeOH).

Step 5. 1-[N-[1(S)-Ethoxycarbonyl-3-(4-ethoxycarbonylphenyl)propyl-(S)-alanyl]-cis,syn-perhydroindole-2(S)-carboxylic acid t-butyl ester: Add cis,syn-perhydroindole-2(S)-carboxylic acid t-butyl ester (1.28 g) in DMF (10 ml) to the product of Step 4 (2.00 g), DEC (1.10 g) and HOBT (0.90 g). Add N-methylmorpholine (0.63 ml) and stir the resulting mixture at room temperature for 20 hr. Concentrate the reaction mixture in vacuo and partition between EtOAc and H$_2$O. Dry (MgSO$_4$) the EtOAc and concentrate in vacuo to give a pale amber residue. Chromatograph this residue on a column of silica gel (2L), eluting with EtOAc:hexane 1:1 to give the title compound, a colorless oil (2.48 g), $[\alpha]_D^{26} = -52.4°$ (MeOH).

Step 6. 1-[N-[1(S)-Ethoxycarbonyl-3-(4-ethoxycarbonylphenyl)propyl]-(S)-alanyl]-cis,syn-perhydroindole-2(S)-carboxylic acid: Treat the product of Step 5 (2.40 g) in CH$_2$Cl$_2$ (40 ml) at 0°–5° with TFA (25 ml). Stir for 0.5 hr., warm to room temperature and stir for 6 hr. Concentrate the reaction mixture in vacuo and chromatograph the residue on a column of silica gel (2 L), eluting with CHCl$_3$: i-PrOH:7% NH$_4$OH (1:1:1, organic phase) to give the title compound, a white foam (2.09 g), $[\alpha]_D^{26} = -24.4°$ (MeOH).

EXAMPLE 5

1-[N-[1(S)-Carboxy-3-(4-carboxyphenyl)propyl]-(S)-alanyl]-cis,syn-perhydroindole-2(S)-carboxylic acid Treat the product of Example 5 (1.01 g) in MeOH (40 ml) at 0°–5° with 1N NaOH (6.0 ml) for 2 hr. Warm the mixture to room temperature and stir for 18 hr. Concentrate the mixture under nitrogen to approximately 10 ml and dilute with H$_2$O (10 ml). Stir for 4 hr., cool the reaction mixture to 0°–5° and treat with 1N HCl to give the title compound, a white solid (0.81 g), $[\alpha]_D^{26} = -35.6°$ (MeOH:1N NaOH 3:1).

The compounds of this invention are useful in view of their pharmacological properties. In particular, they possess activity as antihypertensive agents as evidenced by their ability to reduce blood pressure in mammals, including humans, in which the blood pressure has become abnormally elevated.

The compounds of the present invention can be combined with pharmaceutical carriers and administered in a variety of well known pharmaceutical forms suitable for oral and parenteral administration to provide compositions useful in the treatment of cardiovascular disorders and particularly mammalian hypertension.

The effective dose (ED$_{50}$) of the compounds of this invention will typically be in the range of about 0.01 to about 30 mg/kg, preferably about 0.1 to about 10 mg/kg, of mammalian weight, administered in single or divided doses. The exact dose to be administered is dependent upon where the particular compound lies within the above quoted range, as well as upon the age, weight and condition of the individual.

Generally, in treating humans, the compounds of this invention may be administered to ptients in need of such treatment in a dosage range of 5 to 500 mg per patient generally given several times, thus giving a total daily dose of from 5 to 2000 mg per day. Also, the compounds of this invention may be given in combination with diuretics or other antihypertensives. Typically, these are combinations whose individual per day dosages range from one-fifth of the minimally recommended clinical dosages to the maximum recommended levels for the entities when they are given singly. Examples of such diuretics or other antihypertensives are hydrochlorothiazide, chlorothiazide, ethacrynic acid, amiloride, furosemide, propanolol, timolol and methyldopa.

The composition containing the compounds of this invention will preferably contain from about 5 to about 250 mg of the active compound per dosage unit. These compositions are most preferably administered orally. Typical formulations for oral administration are those such as tablets, capsules, syrups, elixirs or suspensions. Typical injectable formulations include solutions and suspensions.

Typical acceptable pharmaceutical carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tri-calcium phosphate; sodium sulfate; calcium sulfate; polyvinylpyrrolidone; polyvinyl alcohol; stearic acid; alkaline earth metal stearates such as magnesium stearate and calcium stearate; stearic acid; vegetable oils such as peanut oil, cottonseed oil, sesame oil, olive oil and corn oil; non-ionic, cationic and anionic surfactants; ethylene glycol polymers; betacyclodextrin; fatty alcohols and hydrolyzed cereal solids; as well as other non-toxic compatible fillers, binders, disintegrants, buffers, preservatives, antioxidants, lubricants, flavoring agents, and the like commonly used in pharmaceutical formulations.

The following examples describe in detail compositions that are illustrative of the present invention. It will be apparent to those skilled in the art that many modifications, both of materials and methods, may be practiced without departing from the purpose and intent of this disclosure.

In the following examples, the active ingredient is one of the compounds previously named.

EXAMPLE 6

| Capsule | Amount (mg) | |
|---|---|---|
| Active ingredient | 250.0 | 125.0 |
| Lactose | 173.0 | 86.5 |
| Corn Starch | 75.0 | 37.5 |
| Magnesium Stearate | 2.0 | 1.0 |
| | 500.0 | 250.0 |

Blend the active ingredient, lactose and corn starch until uniform; then blend the magnesium stearate into the resulting powder. Encapsulate the mixture into suitable sized two-piece hard gelatin capsules.

EXAMPLE 7

| Tablet | Amount (mg) | |
|---|---|---|
| Active ingredient | 250.0 | 125.0 |
| Lactose | 161.0 | 80.5 |
| Corn Starch | 12.0 | 6.0 |
| Water (per thousand tablets) | 120 ml (evaporates) | 60 ml (evaporates) |
| Corn Starch | 75.0 | 37.5 |
| Magnesium Stearate | 2.0 | 1.0 |
| | 500.0 | 250.0 |

Blend the active ingredient with the lactose until uniform. Blend the smaller quantity of corn starch with the water and add the resulting corn starch paste, then mix until a uniform wet mass is formed. Add the remaining corn starch to the remaining wet mass and mix until uniform granules are obtained. Screen the granules through a suitable milling machine, using a ¾ inch stainless steel screen. Dry the milled granules in a suitable drying oven until the desired moisture content is obtained. Mill the dried granules through a suitable milling machine using a 16 mesh stainless steel screen. Blend in the magnesium stearate and compress the resulting mixture into tablets of desired shape, thickness, hardness and disintegration.

EXAMPLE 8

| Injectable Solution | mg/ml |
|---|---|
| Active ingredient | 5.00 |
| Methyl p-hydroxybenzoate | 0.80 |
| Propyl p-hydroxybenzoate | 0.10 |
| Disodium Edetate | 0.10 |
| Citric Acid Monohydrate | 0.08 |
| Dextrose | 40.0 |
| Water for injection qs. ad. | 1.0 ml |

Dissolve the p-hydroxybenzoates in a portion of water for injection at 60°–70° C. and cool the solution to 25°–35° C. Charge and dissolve all other excipients and the active ingredient. Bring the solution to final volume, filter it through a sterilizing membrane and fill into sterile containers.

We claim:

1. A compound represented by the formula

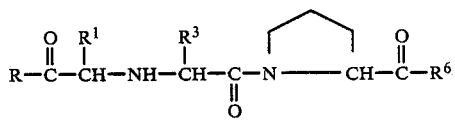

and the pharmaceutically acceptable salts thereof, wherein R and $R^6$ are the same or different and are hydroxy or lower alkoxy;

$R^1$ is benzyloxylower alkyl or benzylthiolower alkyl; and $R^3$ is hydrogen, lower alkyl or aminolower alkyl.

2. A compound of claim 1 wherein R is lower alkoxy.
3. A compound of claim 1 wherein R is ethoxy.
4. A compound of claim 1 wherein $R^6$ is hydroxy.
5. A compound of claim 1 wherein $R^3$ is lower alkyl.
6. A compound of claim 1 wherein $R^3$ is methyl.

7. A compound of claim 1 wherein $R^1$ is benzyloxymethyl.

8. A compound of claim 1 wherein $R^1$ is benzylthiomethyl.

9. A compound of claim 1 wherein R is lower alkoxy, $R^6$ is hydroxy, $R^3$ is lower alkyl, and $R^1$ is benzyloxymethyl or benzylthiomethyl.

10. A compound of claim 9 wherein R is ethoxy and $R^3$ is methyl.

11. A compound of claim 10 which is N-(1(R)-ethoxycarbonyl-2-benzylthioethyl)-(R,S)-alanyl-(S)-proline.

12. A compound of claim 10 which is N-(1(S)-ethoxycarbonyl-2-benzyloxyethyl)-R,S)-alanyl-(S)-proline.

13. An antihypertensive pharmaceutical composition comprising an antihypertensive effective amount of a compound of claim 1, together with a phartmaceutically acceptable carrier.

14. A method for reducing blood pressure in a hypertensive mammal which comprises administering to such a mammal a composition of claim 13.

* * * * *